United States Patent
Hirota et al.

(10) Patent No.: US 9,486,144 B2
(45) Date of Patent: *Nov. 8, 2016

(54) PHOTOACOUSTIC IMAGE GENERATION APPARATUS AND ACOUSTIC WAVE UNIT

(71) Applicant: FUJIFILM Corporation, Tokyo (JP)

(72) Inventors: Kazuhiro Hirota, Kanagawa (JP); Tadashi Kasamatsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 13 days.

This patent is subject to a terminal disclaimer.

(21) Appl. No.: 14/167,808

(22) Filed: Jan. 29, 2014

(65) Prior Publication Data

US 2014/0148682 A1    May 29, 2014

Related U.S. Application Data

(63) Continuation of application No. PCT/JP2012/068904, filed on Jul. 26, 2012.

(30) Foreign Application Priority Data

Jul. 29, 2011    (JP) .................................. 2011-166978
Jul. 19, 2012    (JP) .................................. 2012-160427

(51) Int. Cl.
*A61B 5/05* (2006.01)
*A61B 5/00* (2006.01)
(Continued)

(52) U.S. Cl.
CPC ............... *A61B 5/0095* (2013.01); *A61B 8/13* (2013.01); *H01S 3/106* (2013.01); *A61B 5/14542* (2013.01);
(Continued)

(58) Field of Classification Search
CPC ............ A61B 5/0095; A61B 5/14542; A61B 8/0891; A61B 8/13; A61B 8/463; A61B 8/5207; A61B 8/5261; A61B 8/54; H01S 3/08027; H01S 3/092; H01S 3/106; H01S 3/11
See application file for complete search history.

(56) References Cited

U.S. PATENT DOCUMENTS 4,272,733 A *  6/1981  Walling et al. .................. 372/20
4,809,283 A *  2/1989  Harter ............................. 372/41
(Continued)

FOREIGN PATENT DOCUMENTS

CN    102095685 A    6/2011
JP    10-065260 A    3/1998
(Continued)

OTHER PUBLICATIONS

Extended European Search Report, dated Feb. 27, 2015, for European Application No. 12820334.6.
(Continued)

*Primary Examiner* — Jonathan Cwern
(74) *Attorney, Agent, or Firm* — Birch, Stewart, Kolasch & Birch, LLP

(57) ABSTRACT

Using a laser source unit, pulse laser beams having a plurality of wavelengths is switched and emitted. A Q switch is inserted into an optical resonator including a pair of mirrors which face each other with a laser rod interposed therebetween. A wavelength selection unit includes a plurality of band pass filters having different transmission wavelengths, and selectively inserts the plurality of band pass filters into a light path of the optical resonator. A trigger control circuit controls driving unit that drives the wavelength selection unit so that the band pass filters inserted into the light path of the optical resonator are switched at a predetermined switching speed. In addition, the trigger control circuit causes the laser rod to be irradiated with excitation light from a flash lamp, and then turns on the Q switch at a timing when the wavelength selection unit inserts the band pass filter.

5 Claims, 11 Drawing Sheets

(51) Int. Cl.
*A61B 8/13* (2006.01)
*H01S 3/106* (2006.01)
*A61B 8/08* (2006.01)
*A61B 5/145* (2006.01)
*A61B 8/00* (2006.01)
*H01S 3/08* (2006.01)
*H01S 3/092* (2006.01)
*H01S 3/11* (2006.01)

(52) U.S. Cl.
CPC .............. *A61B 8/0891* (2013.01); *A61B 8/463* (2013.01); *A61B 8/5207* (2013.01); *A61B 8/5261* (2013.01); *A61B 8/54* (2013.01); *H01S 3/08027* (2013.01); *H01S 3/092* (2013.01); *H01S 3/11* (2013.01)

(56) References Cited

U.S. PATENT DOCUMENTS

| | | | |
|---|---|---|---|
| 5,175,736 A * | 12/1992 | Woodward et al. | 372/20 |
| 6,979,292 B2 | 12/2005 | Kanayama et al. | |
| 2003/0072333 A1 * | 4/2003 | Jacobowitz et al. | 372/20 |
| 2003/0118060 A1 * | 6/2003 | Spuehler et al. | 372/18 |
| 2005/0187471 A1 * | 8/2005 | Kanayama et al. | 600/437 |
| 2009/0178099 A1 * | 7/2009 | Chang et al. | 725/118 |
| 2011/0112391 A1 | 5/2011 | Nishihara et al. | |
| 2014/0148680 A1 * | 5/2014 | Kasamatsu et al. | 600/407 |
| 2014/0148681 A1 * | 5/2014 | Hirota et al. | 600/407 |

FOREIGN PATENT DOCUMENTS

| | | |
|---|---|---|
| JP | 2007-81065 A | 3/2007 |
| JP | 2010-046215 A | 3/2010 |

OTHER PUBLICATIONS

A High-Speed Photoacoustic Tomography System based on a Commercial Ultrasound and a Custom Transducer Array, Xueding Wang, Jonathan Cannata, Derek DeBusschere, Changhong Hu, J. Brian Fowlkes, and Paul Carson, Proc. SPIE vol. 7564, 756424 (Feb. 23, 2010).

International Search Report, mailed Jul. 26, 2012, issued in PCT/JP2012/068904.

Written Opinion of the International Search Authority, mailed Jul. 26, 2012, issued in PCT/JP2012/068904.

Notice of Reasons for Allowance dated Jul. 3, 2015 for Chinese Application No. 201280037135.4.

* cited by examiner

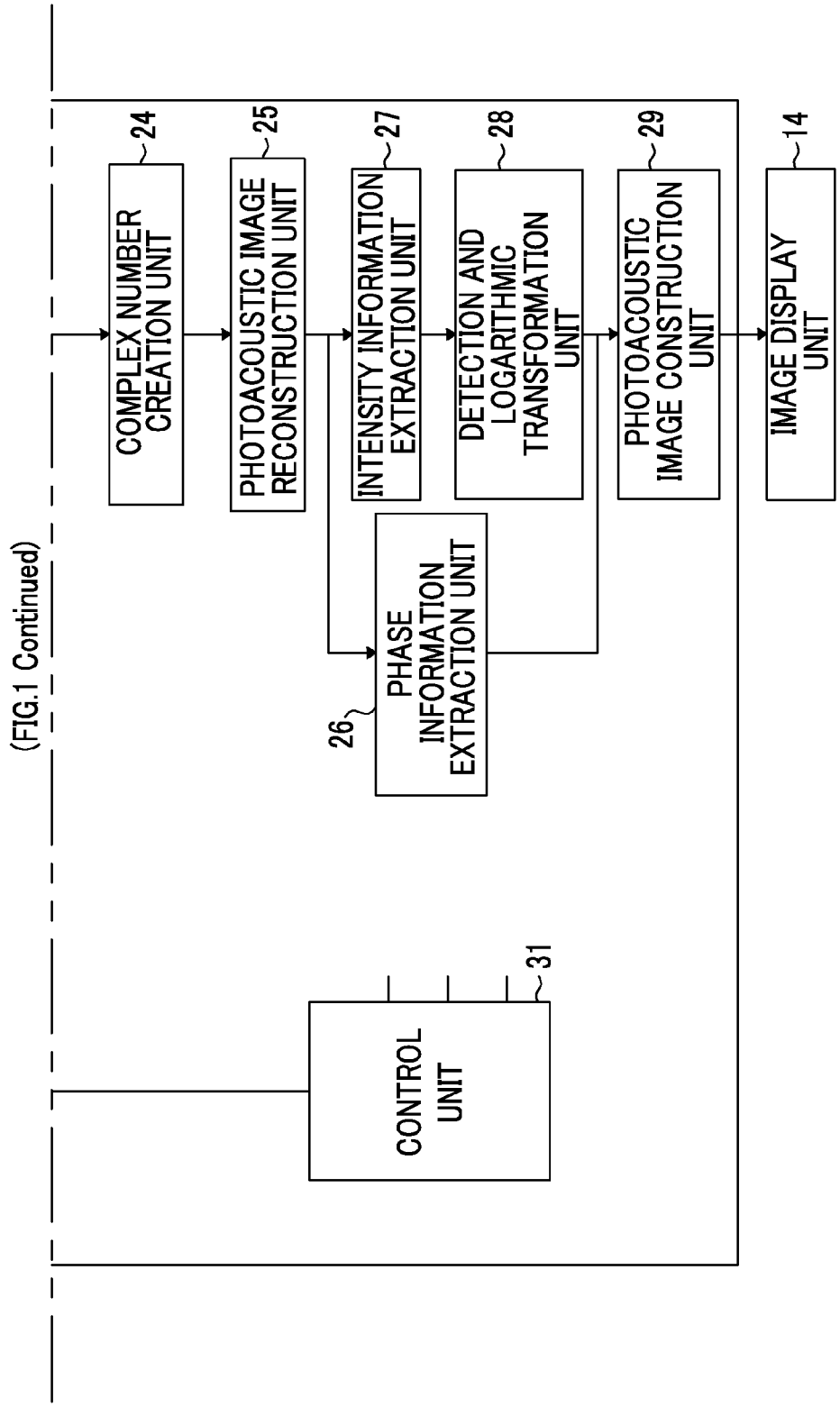

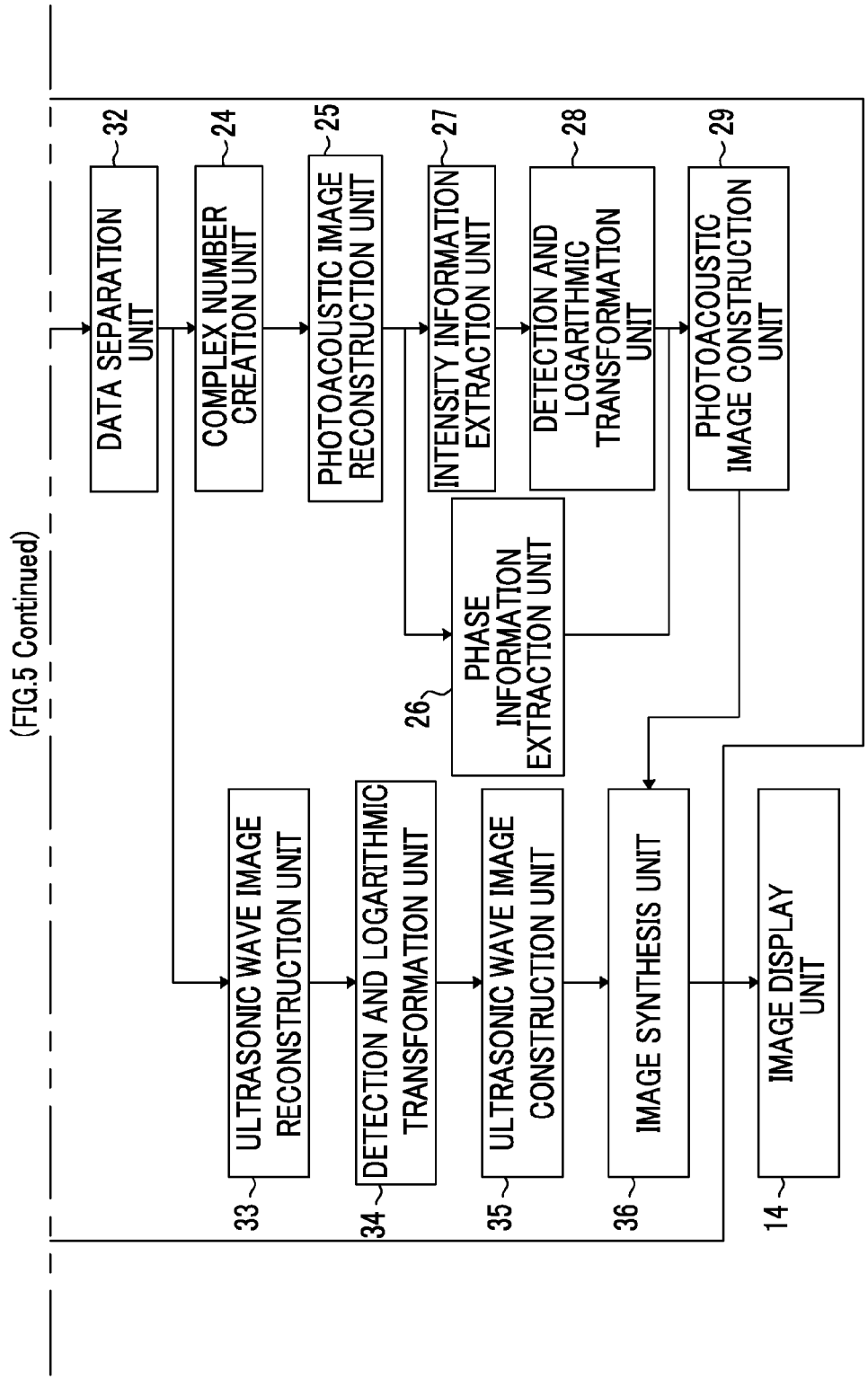
(FIG.5 Continued)

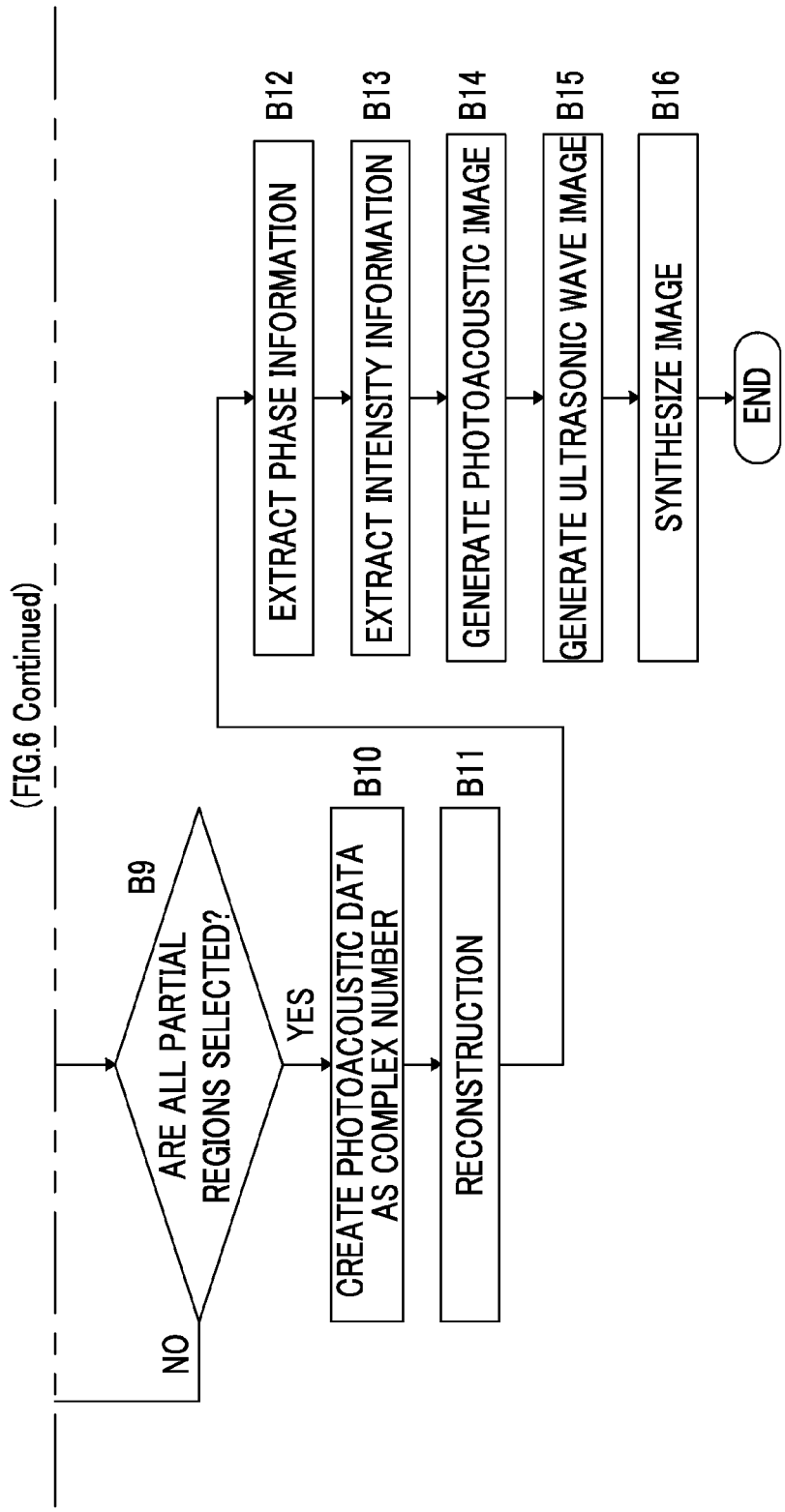

PHOTOACOUSTIC IMAGE GENERATION APPARATUS AND ACOUSTIC WAVE UNIT

CROSS REFERENCE TO RELATED APPLICATIONS

This application is a Continuation of PCT International Application No. PCT/JP2012/068904 filed on Jul. 26, 2012, which claims priority under 35 U.S.C §119(a) to Patent Application No. 2011-166978 filed in Japan on Jul. 29, 2011 and Patent Application No. 2012-160427 filed in Japan on Jul. 19, 2012, all of which are hereby expressly incorporated by reference into the present application.

BACKGROUND OF THE INVENTION

1. Field of the Invention

The present invention relates to a photoacoustic image generation apparatus and an acoustic wave unit, and more particularly, to a photoacoustic image generation apparatus, which when a test object is irradiated with laser beams having a plurality of wavelengths, generates a photoacoustic image on the basis of photoacoustic signals detected with respect to the respective wavelengths, and an acoustic wave unit.

2. Description of the Related Art

Hitherto, for example, as disclosed in JP2005-21380A and A High-Speed Photoacoustic Tomography System based on a Commercial Ultrasound and a Custom Transducer Array, Xueding Wang, Jonathan Cannata, Derek DeBusschere, Changhong Hu, J. Brian Fowlkes, and Paul Carson, Proc. SPIE Vol. 7564, 756424 (Feb. 23, 2010), a photoacoustic image forming apparatus that forms an image of the inside of a living body using a photoacoustic effect has been known. In the photoacoustic image forming apparatus, a living body is irradiated with pulsed light such as a pulse laser beam. Body tissues absorbing energy of the pulsed light expand in volume inside the living body irradiated with the pulsed light, and thus acoustic waves are generated. It is possible to detect the acoustic waves using an ultrasonic probe or the like, and to form a visible image of the inside of the living body on the basis of the detected signal (photoacoustic signal). In a photoacoustic image forming method, acoustic waves are generated in a specific light absorber, and thus it is possible to form an image of specific tissues in the living body, for example, blood vessels.

Incidentally, many of body tissues have an optical absorption property varying depending on a wavelength of light, and generally, the optical absorption property is unique for each tissue. For example, FIG. 8 illustrates molecular absorption coefficients of oxygenated hemoglobin (hemoglobin combined with oxygen: oxy-Hb) which is contained in a large amount in an artery of a human and deoxygenated hemoglobin (hemoglobin not combined with oxygen: deoxy-Hb) which is contained in a large amount in a vein, according to light wavelengths. An optical absorption property of an artery corresponds to that of oxygenated hemoglobin, and an optical absorption property of a vein corresponds to that of deoxygenated hemoglobin. There is known a photoacoustic image forming method of irradiating blood vessel parts with light beams having two different types of wavelengths and of distinctively forming images of an artery and a vein (for example, see JP2010-046215A), using a difference in light absorptivity according to the wavelengths.

Here, with regard to a variable wavelength laser, JP-1998-65260A (JP-H10-65260A) discloses a multicolor solid laser apparatus capable of easily switching and outputting laser beams having a plurality of types of wavelengths. In JP-1998-65260A (JP-H10-65260A), a filter selectively transmitting only light with a specific peak wavelength is disposed on a light path with one of a laser active medium and an optical resonator mirror. As many filters as peak wavelengths to be selected are prepared, and any one of the prepared filters is disposed on the light path, thereby allowing laser beams having a plurality of wavelengths to be switched and emitted.

SUMMARY OF THE INVENTION

In photoacoustic imaging, when a photoacoustic image is generated across a plurality of frames, a test object may be attempted to be continuously irradiated with, for example, a plurality of sets of pulse laser beams having two wavelengths for each set. As disclosed in JP-1998-65260A (JP-H10-65260A), a wavelength of a laser beam is simply switched by switching a filter inserted into a light path. Moreover, JP-1998-65260A (JP-H10-65260A) do not disclose means for continuously switching and emitting laser beams having a plurality of wavelengths. In addition, JP-1998-65260A (JP-H10-65260A) do not disclose means for controlling a wavelength of a laser beam emitted by a laser light source from the outside of the laser light source.

The present invention is contrived in view of such situations, and an object thereof is to provide an acoustic wave unit capable of switching and emitting laser beams having a plurality of wavelengths from the outside of a laser light source in photoacoustic imaging, and a photoacoustic image generation apparatus including the acoustic wave unit.

In order to achieve the above-described object, the present invention provides a photoacoustic image generation apparatus including: a laser source unit capable of emitting a plurality of pulse laser beams having different wavelength respectively, the laser source unit including a laser rod, an excitation light source that irradiates the laser rod with excitation light, an optical resonator having a pair of mirrors facing each other with the laser rod interposed therebetween, a Q switch which is inserted into the optical resonator, wavelength selection unit that includes a plurality of band pass filters having different transmission wavelengths and selectively inserts the plurality of band pass filters into a light path of the optical resonator, and driving unit that drives the wavelength selection unit so that the band pass filters inserted into the light path of the optical resonator are sequentially switched in a predetermined order; and an acoustic wave unit that generates a photoacoustic image, the acoustic wave unit including detection unit that detects a photoacoustic signal generated within an object when the object is irradiated with the pulse laser beam having the plurality of wavelengths, and generates pieces of photoacoustic data corresponding to the respective wavelengths, intensity ratio extraction unit that extracts a magnitude relation between relative signal intensities of the pieces of photoacoustic data corresponding to the respective wavelengths, photoacoustic image construction unit that generates a photoacoustic image on the basis of the extracted magnitude relation, and a trigger control circuit that causes the laser rod to be irradiated with excitation light from the excitation light source while controlling the driving unit so that the band pass filters inserted into the light path of the optical resonator are switched at a predetermined switching speed, and after the irradiation with the excitation light, turns on the Q switch at a timing when the wavelength selection unit inserts the band pass filter, having a transmission wavelength corresponding to a wavelength of the pulse laser beam to be emitted, into the light path to emit the pulse laser beam.

Moreover, in the present invention, the wavelength selection unit may be constituted by a filter rotating body that switches the band pass filter selectively inserted into the light path of the optical resonator in association with rotational displacement, and the driving unit may rotationally drive the filter rotating body.

Further, it is preferable that the trigger control circuit control the driving unit so that the filter rotating body is continuously rotated in a predetermined direction at a predetermined rotation speed.

Yet further, the predetermined rotation speed may be determined on the basis of the number of wavelengths of the pulse laser beam to be emitted and the number of times of emission of the pulse laser beam per unit time.

Furthermore, the trigger control circuit may determine timing at which irradiation with the excitation light is performed and timing at which the Q switch is turned on, on the basis of filter state information indicating a rotational displacement position of the filter rotating body.

Moreover, when the filter state information is set to information indicating a position obtained by subtracting the amount of rotational displacement of the filter rotating body during a period of time required for the excitation of the laser rod from a position of the filter rotating body at which the band pass filter corresponding to a wavelength of the pulse laser beam to be emitted is inserted into the light path, the trigger control circuit may cause the laser rod to be irradiated with excitation light.

Further, the trigger control circuit may control the driving unit so that the amount of change in the filter state information during a predetermined period of time is set to the amount of change depending on the predetermined rotation speed.

Yet further, the laser source unit may further include a rotation control unit that controls the driving unit so that the amount of rotational displacement of the filter rotating body during a predetermined period of time is set to an amount depending on the predetermined rotation speed, and the trigger control circuit may control the driving unit through the rotation control unit.

Furthermore, acoustic wave unit may further include intensity information extraction unit that generates intensity information indicating signal intensity on the basis of the pieces of photoacoustic data corresponding to the respective wavelengths. The photoacoustic image construction unit may determine a gradation value of each pixel of the photoacoustic image on the basis of the intensity information, and may determine a display color of each pixel on the basis of the extracted magnitude relation.

Moreover, the plurality of wavelengths of the pulse laser beam to be emitted by the laser source unit may include a first wavelength and a second wavelength. The acoustic wave unit may further include complex number creation unit that generates complex number data in which one of first photoacoustic data corresponding to a photoacoustic signal, detected when irradiation with the pulse laser beam having the first wavelength is performed, and second photoacoustic data corresponding to a photoacoustic signal, detected when irradiation with the pulse laser beam having the second wavelength is performed, is set to a real part and the other one is set to an imaginary part, and photoacoustic image reconstruction unit that generates a reconstructed image from the complex number data using a Fourier transform method. The intensity ratio extraction unit may extract phase information as the magnitude relation from the reconstructed image, and the intensity information extraction unit may extract the intensity information from the reconstructed image.

Further, the detection unit may further detect reflected acoustic waves with respect to acoustic waves transmitted to the object to generate reflected acoustic wave data, and the acoustic wave unit may further include acoustic wave image generation unit that generates an acoustic wave image on the basis of the reflected acoustic wave data.

The wavelength selection unit may be a rotating body in which the plurality of band pass filters are disposed in a circumferential shape.

The wavelength selection unit may be configured in such a manner that the plurality of band pass filters are disposed on a straight line, and the driving unit may cyclically insert the plurality of band pass filters into a light path of the optical resonator.

The wavelength selection unit may be configured in such a manner that the plurality of band pass filters are disposed on a straight line, and the driving unit may reciprocate the wavelength selection unit to cause the plurality of band pass filters to cross the light path of the optical resonator.

Moreover, in order to achieve the above-described object, the present invention also provides an acoustic wave unit including: detection unit that detects a photoacoustic signal generated within an object when the object is irradiated with pulse laser beams having a plurality of different wavelengths, and generates pieces of photoacoustic data corresponding to the respective wavelengths; intensity ratio extraction unit that extracts a magnitude relation between relative signal intensities of the pieces of photoacoustic data corresponding to the respective wavelengths; photoacoustic image construction unit that generates a photoacoustic image on the basis of the extracted magnitude relation; and a trigger control circuit that causes a laser rod to be irradiated with excitation light from an excitation light source while controlling driving unit driving a wavelength selection unit, including a plurality of band pass filters having different transmission wavelengths, so as to switch the band pass filters inserted into a light path of an optical resonator at a predetermined switching speed, so that the plurality of band pass filters are selectively inserted into the light path of the optical resonator, including a pair of mirrors facing each other with the laser rod interposed therebetween, in a predetermined order, and after the irradiation with the excitation light, turns on a Q switch inserted into the optical resonator at a timing when the wavelength selection unit inserts the band pass filter, having the transmission wavelength corresponding to a wavelength of the pulse laser beam to be emitted, into the light path to cause the pulse laser beam to be emitted.

Moreover, in a photoacoustic image generation apparatus and an acoustic wave unit of the present invention, a flash lamp is turned on to excite a laser rod while driving wavelength selection unit including a plurality of band pass filters having different transmission wavelengths so that the plurality of band pass filters selectively inserted into a light path of an optical resonator are switched at a predetermined speed. After the excitation of the laser rod, when the band pass filter transmitting light having a wavelength of the pulse laser beam to be emitted is inserted into the light path of the optical resonator, a Q switch is turned on. For example, wavelength selection unit including two band pass filters having different transmission wavelengths is continuously driven, and thus it is possible to continuously and selectively insert the two band pass filters into a light path of an optical resonator and to continuously switch and emit pulse laser beams having a plurality of different wavelengths from a laser source unit. In addition, in the present invention, when the Q switch is turned on, the wavelength of the pulse laser beam is determined according to which band pass filter is inserted into the light path of the optical resonator, and it is possible to control the wavelength of the pulse laser beam emitted by the laser source unit from the acoustic wave unit side. Furthermore, in the present invention, the acoustic wave unit determines an emission timing of the pulse laser beam, and thus it is not necessary to acquire a signal such as a synchronization signal indicating laser emission from the laser source unit, in the start of sampling of a photoacoustic signal.

DESCRIPTION OF THE PREFERRED EMBODIMENTS

Figure 1:
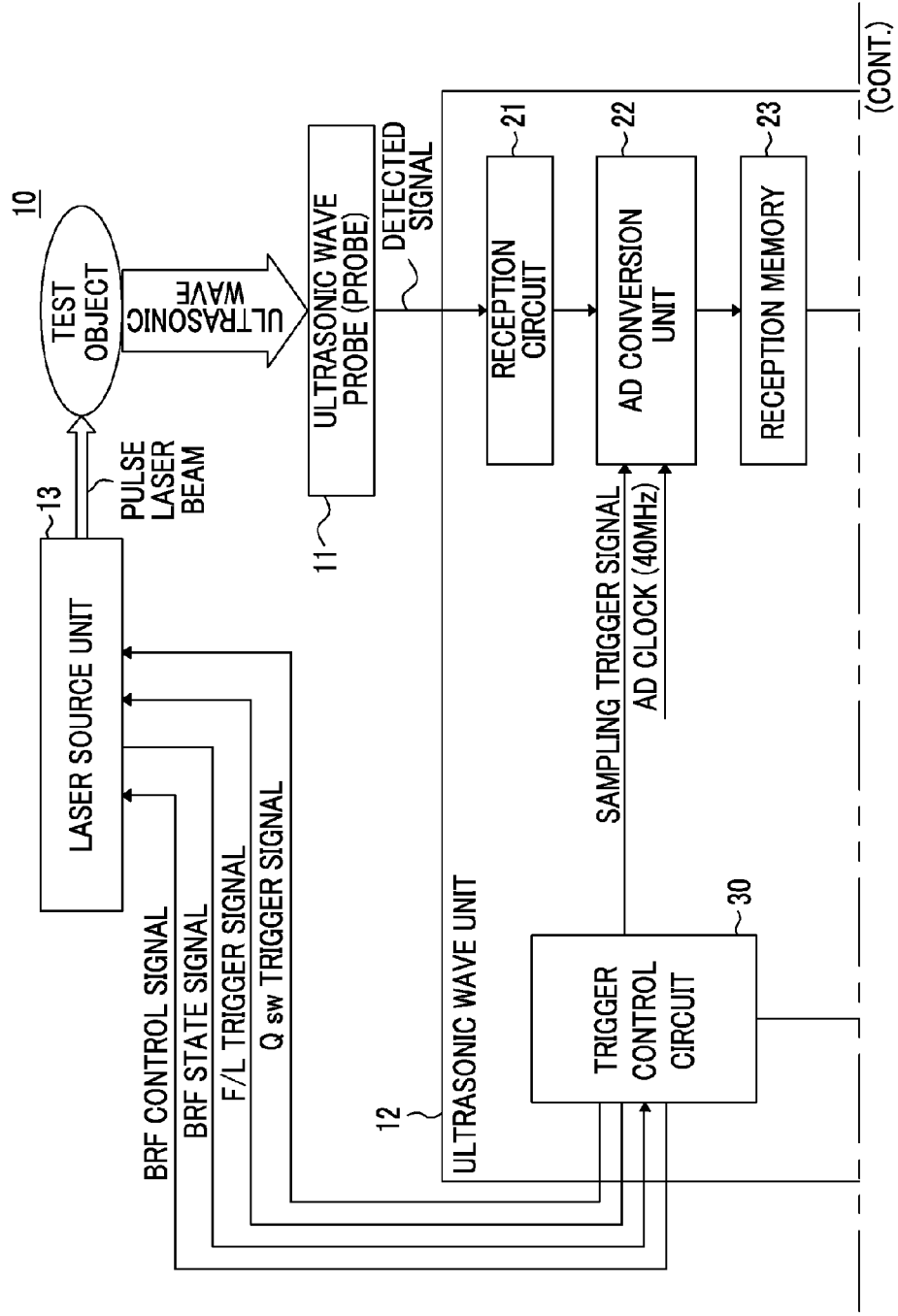
FIG. 1 is a block diagram of a photoacoustic image generation apparatus according to a first embodiment of the present invention.

Hereinafter, embodiments of the present invention will be described in detail with reference to the accompanying drawings. Note that, in examples of the present invention, ultrasonic waves are used as acoustic waves, but the acoustic waves may be acoustic waves having an audible frequency by selecting an appropriate frequency according to an object to be tested or measurement conditions. FIG. 1 illustrates a photoacoustic image generation apparatus according to a first embodiment of the present invention. A photoacoustic image generation apparatus 10 includes an ultrasonic wave probe (probe) 11, an ultrasonic wave unit 12, and a laser source unit 13. The laser source unit 13 emits a pulse laser beam with which a test object is to be irradiated. The laser source unit 13 switches and emits pulse laser beams having a plurality of different wavelengths. Hereinafter, a description will be mainly given on the assumption that the laser source unit 13 sequentially emits a pulse laser beam having a first wavelength and a pulse laser beam having a second wavelength.

Figure 8:
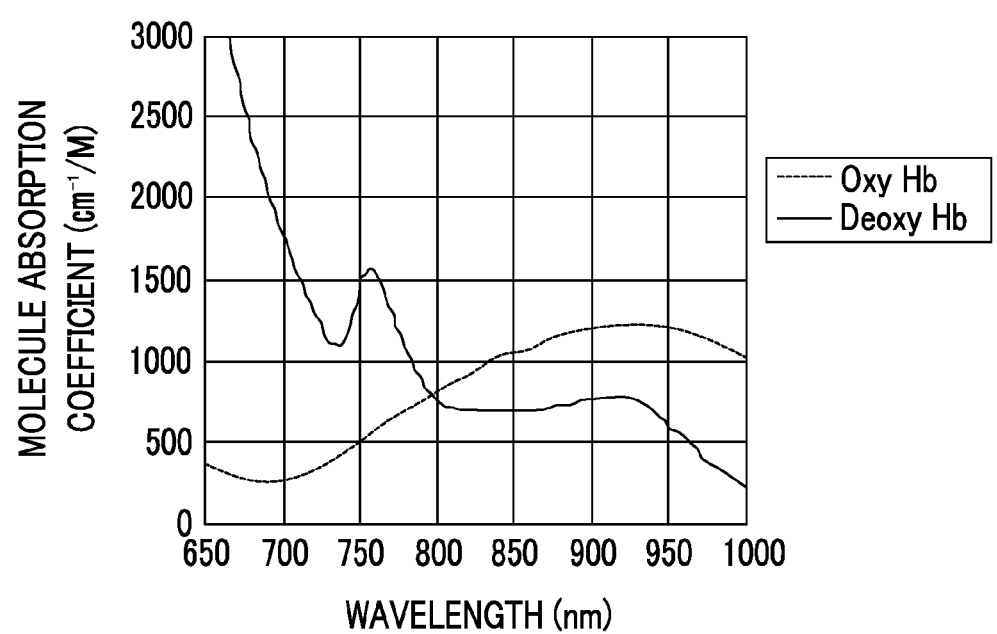
FIG. 8 is a graph illustrating molecular absorption coefficients of oxygenated hemoglobin and deoxygenated hemoglobin according to light wavelengths.

For example, a wavelength of approximately 750 nm is considered as the first wavelength (center wavelength), and a wavelength of approximately 800 nm is considered as the second wavelength. Referring to FIG. 8 described above, a molecular absorption coefficient of oxygenated hemoglobin (hemoglobin combined with oxygen: oxy-Hb) which is contained in a large amount in an artery of a human at a wavelength of 750 nm is lower than a molecular absorption coefficient of that at a wavelength of 800 nm On the other hand, a molecular absorption coefficient of deoxygenated hemoglobin (hemoglobin not combined with oxygen: deoxy-Hb) which is contained in a large amount in a vein at a wavelength of 750 nm is higher than a molecular absorption coefficient of that at a wavelength of 800 nm. It is possible to discriminate between a photoacoustic signal from the artery and a photoacoustic signal from the vein by examining whether a photoacoustic signal obtained at the wavelength of 750 nm is relatively larger or smaller than a photoacoustic signal obtained at the wavelength of 800 nm, using such a property.

The pulse laser beam emitted from the laser source unit 13 is guided to a probe 11 using light guiding means such as an optical fiber, and is irradiated toward a test object from the probe 11. An irradiation position of the pulse laser beam is not particularly limited, and the pulse laser beam may be irradiated from any place other than the probe 11. Ultrasonic waves (acoustic waves) are generated within the test object by a light absorber absorbing energy of the irradiated pulse laser beam. The probe 11 includes an ultrasonic wave detector. The probe 11 includes, for example, a plurality of ultrasonic wave detector elements (ultrasonic wave vibrators) which are arranged one-dimensionally, and the acoustic waves (photoacoustic signal) from the inside of the test object are detected by the ultrasonic wave vibrators that are arranged one-dimensionally.

The ultrasonic wave unit 12 includes a reception circuit 21, AD conversion unit 22, a reception memory 23, complex number creation unit 24, photoacoustic image reconstruction unit 25, phase information extraction unit 26, intensity information extraction unit 27, detection and logarithmic transformation unit 28, photoacoustic image construction unit 29, a trigger control circuit 30, and control unit 31. The reception circuit 21 receives a photoacoustic signal detected by the probe 11. The AD conversion unit 22, which is detection unit, samples the photoacoustic signal received by the reception circuit 21 and generates photoacoustic data which is digital data. The AD conversion unit 22 samples the photoacoustic signal in synchronization with an AD clock signal, with a predetermined sampling period.

The AD conversion unit 22 stores photoacoustic data in the reception memory 23. The AD conversion unit 22 stores, in the reception memory 23, photoacoustic data corresponding to the respective wavelengths of the pulse laser beam emitted from the laser source unit 13. In other words, the AD conversion unit 22 stores, in the reception memory 23, first photoacoustic data obtained by sampling a photoacoustic signal detected by the probe 11 when a test object is irradiated with a pulse laser beam having a first wavelength and second photoacoustic data obtained by sampling a photoacoustic signal detected by the probe 11 when the test object is irradiated with a second pulse laser beam.

The complex number creation unit 24 reads out the first photoacoustic data and the second photoacoustic data from the reception memory 23, and generates complex number data in which any one of the first photoacoustic data and the second photoacoustic data is set to a real part and the other one is set to an imaginary part. Hereinafter, a description will be given on the assumption that the complex number creation unit 24 generates complex number data in which the first photoacoustic data is set to a real part and the second photoacoustic data is set to as an imaginary part.

The photoacoustic image reconstruction unit 25 inputs the complex number data from the complex number creation unit 24. The photoacoustic image reconstruction unit 25 performs image reconstruction from the input complex number data using a Fourier transform method (FTA method). A well-known method of the related art which is disclosed in, for example, a document "Photoacoustic Image Reconstruction-A Quantitative Analysis" Jonathan I. Sperl et al. SPIE-OSA, Vol. 6631 663103 can be applied to the image reconstruction using the Fourier transform method. The photoacoustic image reconstruction unit 25 inputs data indicating the reconstructed image through Fourier transformation to the phase information extraction unit 26 and the intensity information extraction unit 27.

The phase information extraction unit 26 extracts a magnitude relation of relative signal intensities between pieces of photoacoustic data corresponding to the respective wavelengths. In this embodiment, the phase information extraction unit 26 sets the reconstructed image reconstructed by the photoacoustic image reconstruction unit 25 as input data. In addition, the phase information extraction unit extracts, when the real part and the imaginary part are compared with each other, phase information indicating how relatively large either of the two parts is. For example, when the complex number data is expressed by X+iY, the phase information extraction unit 26 generates the relation of $\theta=\tan^{-1}(Y/X)$ as phase information. Note that, when the relation of X=0 is satisfied, the relation of $\theta=90°$ is established. When first photoacoustic data (X) constituting the real part is equal to second photoacoustic data (Y) constituting the imaginary part, the phase information satisfies the relation of $\theta=45°$. As the first photoacoustic data becomes relatively large, the phase information becomes closer to the relation of $\theta=0°$. As the second photoacoustic data becomes large, the phase information becomes closer to the relation of $\theta=90°$.

The intensity information extraction unit 27 generates intensity information indicating signal intensity on the basis of the pieces of photoacoustic data corresponding to the respective wavelengths. In this embodiment, the intensity information extraction unit 27 sets the reconstructed image reconstructed by the photoacoustic image reconstruction unit 25 as input data, and generates the intensity information from the input data which is complex number data. For example, when the complex number data is expressed by X+iY, the intensity information extraction unit 27 extracts $(X^2+Y^2)^{1/2}$ as intensity information. The detection and logarithmic transformation unit 28 generates an envelope of data indicating the intensity information extracted by the intensity information extraction unit 27, and then widens a dynamic range by performing logarithmic transformation on the envelope.

The photoacoustic image construction unit 29 inputs the phase information from the phase information extraction unit 26, and inputs the intensity information after the detection and logarithmic transformation process from the detection and logarithmic transformation unit 28. The photoacoustic image construction unit 29 generates a photoacoustic image which is a distribution image of a light absorber, on the basis of the input phase information and intensity information. For example, the photoacoustic image construction unit 29 determines luminance (gradation value) of each pixel in the distribution image of the light absorber, on the basis of the input intensity information. In addition, for example, the photoacoustic image construction unit 29 determines color of each pixel (display color) in the distribution image of the light absorber, on the basis of the phase information. The photoacoustic image construction unit 29 determines color of each pixel on the basis of the input phase information, for example, using the range of phases 0° to 90° in a color map associated with a predetermined color.

Here, since the range of phases 0° to 45° is a range in which the first photoacoustic data is larger than the second photoacoustic data, a generation source of a photoacoustic signal is considered to be a vein through which blood flows, the blood mainly containing deoxygenated hemoglobin in which the amount of absorption of a wavelength of 756 nm is greater than that of a wavelength of 798 nm. On the other hand, since the range of phases 45° to 90° is a range in which the first photoacoustic data is smaller than the second photoacoustic data, the generation source of the photoacoustic signal is considered to be an artery through which blood flows, the blood mainly containing oxygenated hemoglobin in which the amount of absorption of a wavelength of 756 nm is less than that of a wavelength of 798 nm.

Consequently, as the color map, a color map is used in which color gradually changes so as to become blue at the phase of 0° and to become colorless (white) as the phase approaches 45° and in which color gradually changes so as to become red at the phase of 90° and to become white as the phase approaches 45°. In this case, in the photoacoustic image, a portion corresponding to the artery can be expressed by red, and a portion corresponding to the vein can be expressed by blue. Color coding between the portion corresponding to the artery and the portion corresponding to the vein has only to be performed on the basis of the phase information by maintaining a constant gradation value, without using the intensity information. The image display unit 14 displays the photoacoustic image generated by the photoacoustic image construction unit 29 on a display screen.

Figure 2:
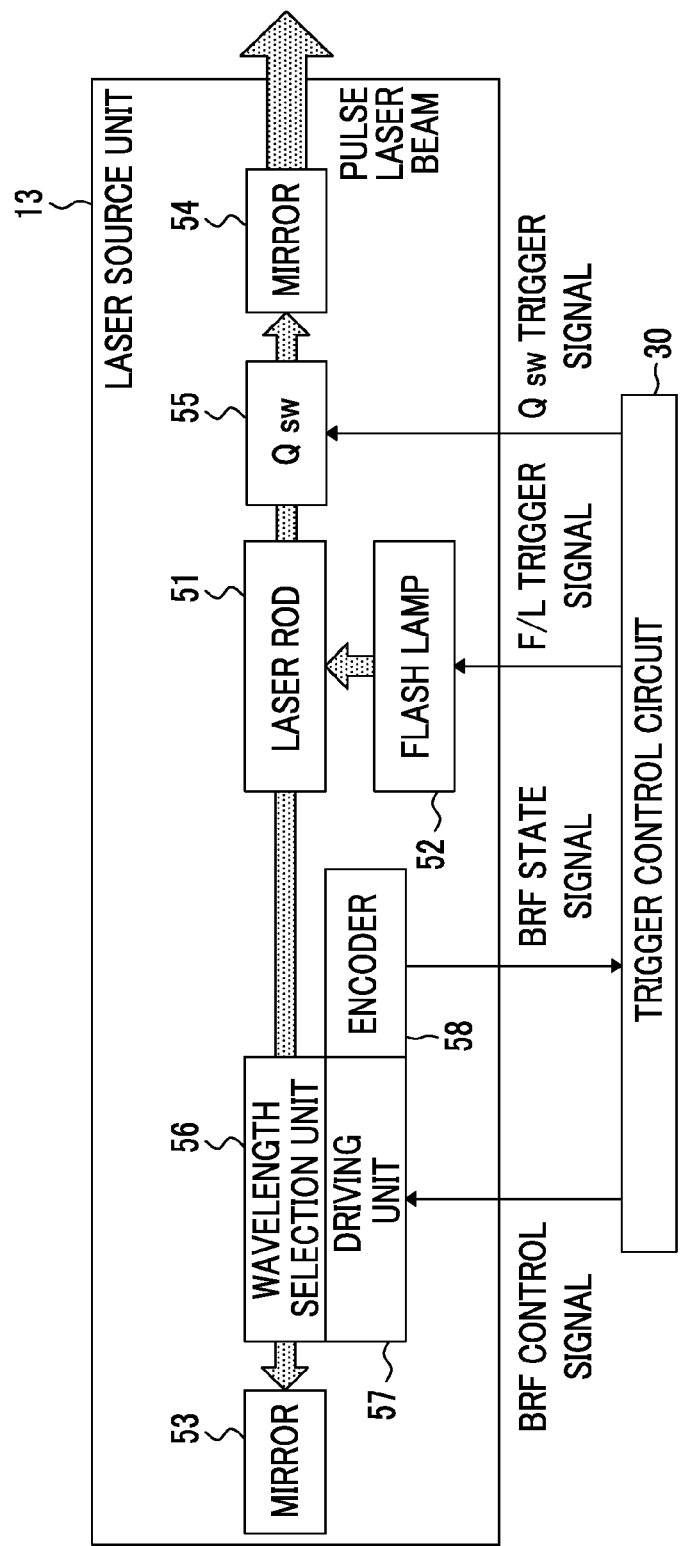
FIG. 2 is a block diagram illustrating a configuration of a laser source unit according to the first embodiment.

Subsequently, a configuration of the laser source unit 13 will be described in detail. FIG. 2 illustrates a configuration of the laser source unit 13. The laser source unit 13 includes a laser rod 51, a flash lamp 52, mirrors 53 and 54, a Q switch 55, wavelength selection unit 56, driving unit 57, and driving state detection unit 58. The laser rod 51 is a laser medium. Examples of the laser rod 51 include alexandrite crystal, Cr:LiSAF(Cr:LiSrAlF6), Cr:LiCAF(Cr:LiCaAlF6) crystal, and Ti:Sapphire crystal. The flash lamp 52 is an excitation light source, and the laser rod 51 is irradiated with excitation light. Any of light sources other than the flash lamp 52, for example, a semiconductor laser or a solid laser may be used as the excitation light source.

The mirrors 53 and 54 face each other with the laser rod 51 interposed therebetween, and an optical resonator is constituted by the mirrors 53 and 54. The mirror 54 is assumed to be the output side. The Q switch 55 is inserted into the optical resonator. An insertion loss within the optical resonator rapidly changes from a high loss (low Q) to a low loss (high Q) by the Q switch 55, and thus a pulse laser beam can be obtained.

The wavelength selection unit 56 includes a plurality of band pass filters (BPF) having different transmission wavelengths. The wavelength selection unit 56 selectively inserts the plurality of band pass filters into a light path of the optical resonator. For example, the wavelength selection unit 56 includes a first band pass filter transmitting light having a wavelength of 750 nm (center wavelength) and a second band pass filter transmitting light having a wavelength of 800 nm (center wavelength). The first band pass filter is inserted into the light path of the optical resonator, and thus it is possible to set the oscillation wavelength of the optical oscillator to 750 nm. In addition, the second band pass filter is inserted into the light path of the optical resonator, and thus it is possible to set the oscillation wavelength of the optical oscillator to 800 nm.

The driving unit 57 drives the wavelength selection unit 56 so that the band pass filters inserted into the light path of the optical resonator are sequentially switched in a predetermined order. For example, when the wavelength selection unit 56 is constituted by a filter rotating body which switches the band pass filter selectively inserted into the light path of the optical resonator in accordance with rotational displacement, the driving unit 57 rotationally drives the filter rotating body constituting the wavelength selection unit 56. The driving state detection unit 58 detects a driving state of the wavelength selection unit 56. For example, the driving state detection unit 58 detects the rotational displacement of the wavelength selection unit 56 which is a filter rotating body. The driving state detection unit 58 outputs BPF state information indicating the rotational displacement position of the filter rotating body to the ultrasonic wave unit 12.

Referring back to FIG. 1, the control unit 31 controls each unit within the ultrasonic wave unit 12. The trigger control circuit 30 controls the driving unit 57 so that the band pass filter inserted into the light path of the optical resonator by the wavelength selection unit 56 within the laser source unit 13 is switched at a predetermined switching speed. For example, the trigger control circuit 30 controls the driving unit 57 so that the filter rotating body constituting the wavelength selection unit 56 is continuously rotated in a predetermined direction at a predetermined rotation speed. For example, the rotation speed of the filter rotating body can be determined on the basis of the number of wavelengths (number of transmission wavelengths of band pass filter) of a pulse laser beam to be emitted from the laser source unit 13 and the number of times of emission of the pulse laser beam per unit time.

The trigger control circuit 30 outputs a BPF control signal for controlling the driving of the wavelength selection unit 56. The driving unit 57 of the laser source unit 13 drives the wavelength selection unit 56 in response to the BPF control signal. For example, the trigger control circuit 30 controls the driving unit 57 so that the amount of change in BPF state information during a predetermined period of time is set to the amount of change depending on a switching speed (rotation speed of filter rotating body) of a predetermined band pass filter, on the basis of the BPF control signal.

In addition to the above description, the trigger control circuit 30 outputs a flash lamp trigger signal for controlling the emission of the flash lamp 52 to the laser source unit 13, and causes the laser rod 51 to be irradiated with excitation light from the flash lamp 52. The trigger control circuit 30 outputs the flash lamp trigger signal on the basis of a BPF state signal. For example, when the BPF state information is set to information indicating the position obtained by subtracting the amount of displacement of the wavelength selection unit 56 during a period of time required for the excitation of the laser rod 51 from the driving position of the wavelength selection unit 56 which inserts the band pass filter, corresponding to the wavelength of the pulse laser beam to be emitted, into the light path of the optical resonator, the trigger control circuit 30 outputs the flash lamp trigger signal and causes the laser rod 51 to be irradiated with excitation light.

After the irradiation with the excitation light, the trigger control circuit 30 outputs a Q switch trigger signal to the Q switch 55 at the timing when the wavelength selection unit 56 inserts the band pass filter having a transmission wavelength, corresponding to the wavelength of the pulse laser beam to be emitted, into the light path of the optical resonator. For example, when the wavelength selection unit 56 is constituted by a filter rotating body, the trigger control circuit 30 outputs the Q switch trigger signal when the BPF state information is set to information indicating that the band pass filter, transmitting light having a wavelength of the pulse laser beam to be emitted, is inserted into the light path of the optical resonator. The Q switch 55 rapidly changes the insertion loss within the optical resonator from a high loss to a low loss (Q switch is turned on) in response to the Q switch trigger signal, and thus the pulse laser beam is emitted from the mirror 54 on the output side.

The trigger control circuit 30 outputs a sampling trigger signal (AD trigger signal) to the AD conversion unit 22 in accordance with the timing of the Q switch trigger signal, that is, the emission timing of the pulse laser beam. The AD conversion unit 22 starts the sampling of a photoacoustic signal on the basis of the sampling trigger signal.

Figure 3:
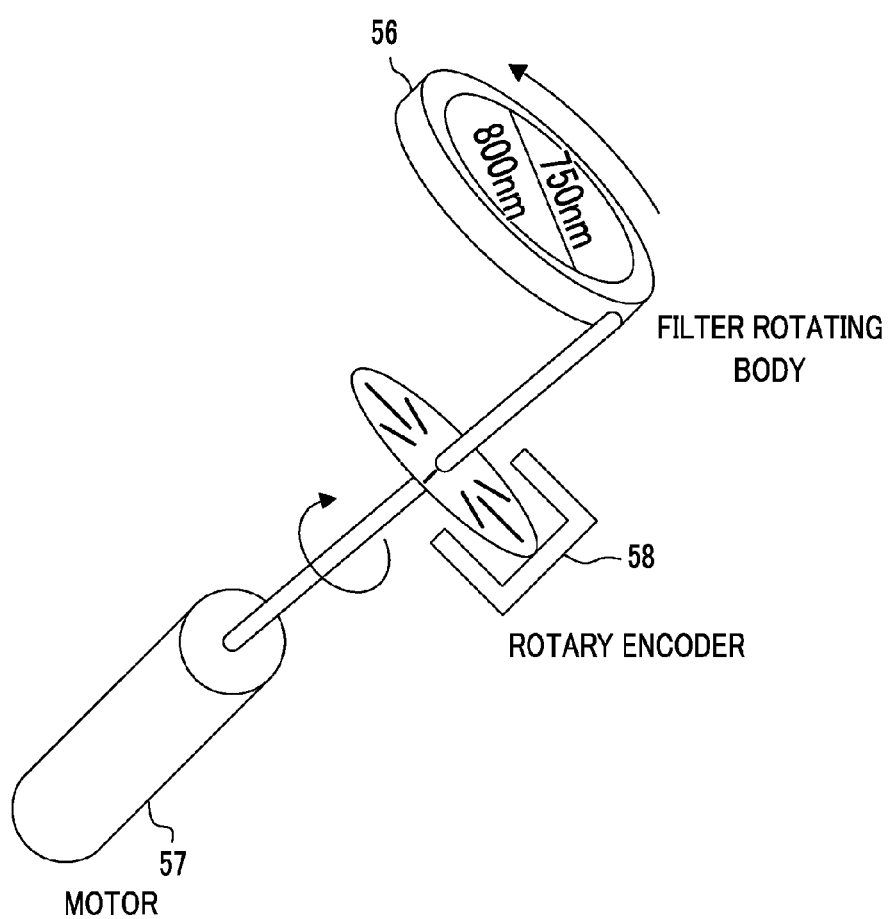
FIG. 3 is a perspective view illustrating a configuration example of wavelength selection unit, driving unit, and driving state detection unit.

FIG. 3 illustrates a configuration example of the wavelength selection unit 56, the driving unit 57, and the driving state detection unit 58. In this example, the wavelength selection unit 56 is a filter rotating body including two band pass filters, and the driving unit 57 is a servo motor. In addition, the driving state detection unit 58 is a rotary encoder. The wavelength selection unit 56 rotates in association with the rotation of an output axis of the servo motor. Half the filter rotating body (for example, rotational displacement position 0° to) 180° which constitutes the wavelength selection unit 56 is the first band pass filter transmitting light having a wavelength of 750 nm, and the other half (for example, rotational displacement position 180° to 360°) thereof is the second band pass filter transmitting light having a wavelength of 800 nm. Such a filter rotating body is rotated, and thus it is possible to alternately insert the first band pass filter and the second band pass filter into the light path of the optical resonator at a switching speed according to the rotation speed of the filter rotating body.

The rotary encoder detects the rotational displacement of the filter rotating body by a rotating plate with a slit which is mounted to the output axis of the servo motor and a transmission-type photointerrupter, and generates the BPF state information. For example, the trigger control circuit 30 monitors the BPF state information, and controls a voltage or the like to be supplied to the servo motor based on the BPF control signal so that the amount of rotational displacement of the rotation axis of the servo motor, which is detected by the rotary encoder during a predetermined period of time is maintained at a predetermined amount, thereby rotating the filter rotating body at a predetermined speed.

Figure 4:
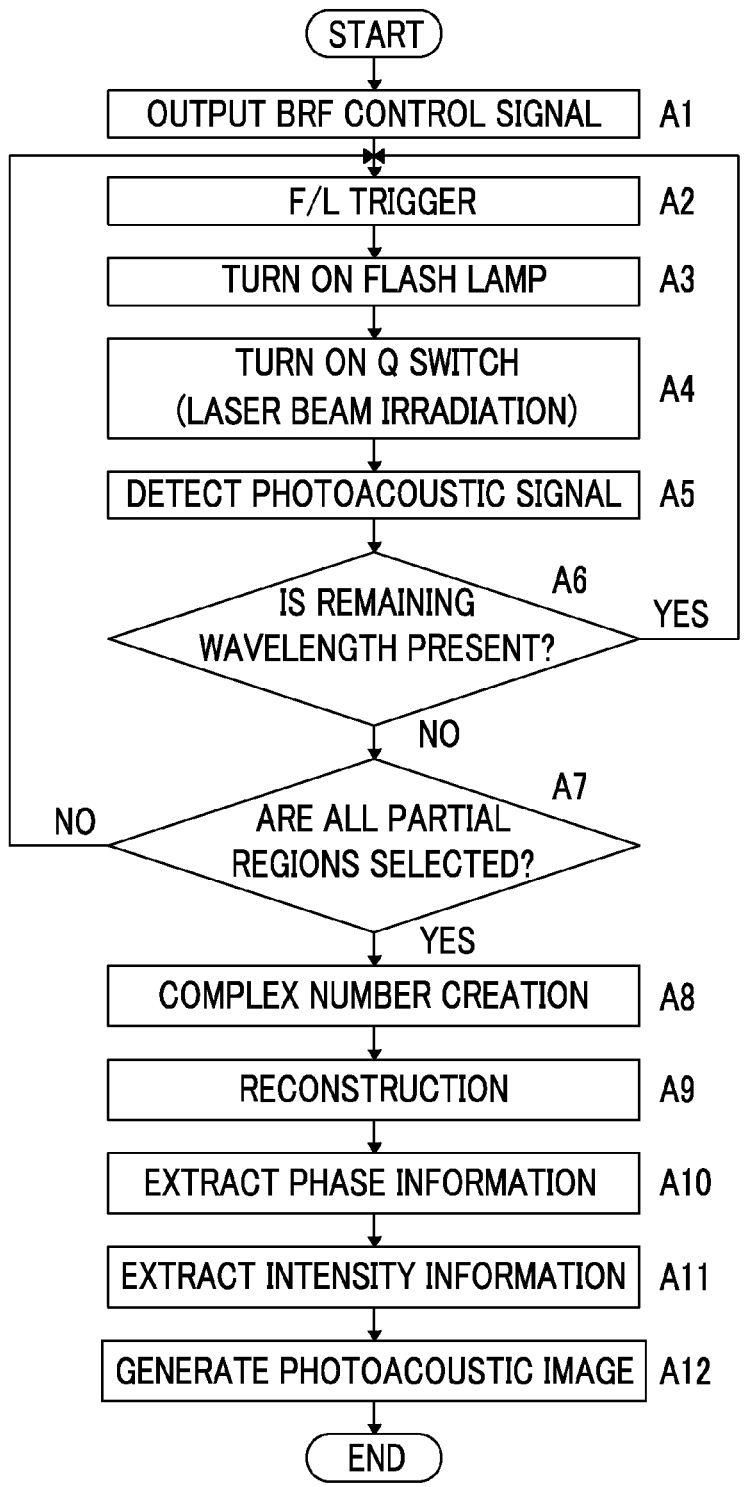
FIG. 4 is a flow chart illustrating an operation procedure of the photoacoustic image generation apparatus according to the first embodiment.

FIG. 4 illustrates an operation procedure of the photoacoustic image generation apparatus 10. Herein, a description will be given on the assumption that a region of a test object which is irradiated with a laser beam is divided into a plurality of partial regions. The trigger control circuit 30 outputs the BPF control signal for rotating the wavelength selection unit (filter rotating body) 56 within the laser source unit 13 at a predetermined rotation speed to the laser source unit 13, prior to the irradiation with the pulse laser beam with respect to the test object (step A1). For example, when the filter rotating body illustrated in FIG. 3 is used and when a pulse laser beam is emitted 24 times per one second, two pulse laser beams having wavelengths of 750 nm and 800 nm can be emitted during one rotation of the filter rotating body, and thus the filter rotating body may be rotated at a rotation speed of 24/2=12 rotations per one second.

When the photoacoustic signal is ready to be received, the trigger control circuit 30 outputs the flash lamp trigger signal to the laser source unit 13 at a predetermined timing in order to emit the pulse laser beam having the first wavelength (for example, 750 nm) (step A2). The flash lamp 52 of the laser source unit 13 is turned on in response to the flash lamp trigger signal, and thus the laser rod 51 starts to be excited (step A3). The trigger control circuit 30 turns on the flash lamp 52 at the timing calculated back from the timing at which the rotational displacement position of the wavelength selection unit 56 is set to the position where the band pass filter transmitting light having a wavelength of 750 nm is inserted into the light path of the optical resonator, on the basis of the BPF state information.

After the flash lamp 52 is turned on, the trigger control circuit 30 turns on the Q switch 55 at the timing when the rotational displacement position of the wavelength selection unit 56 is set to the position where the band pass filter transmitting light having a wavelength of 750 nm is inserted into the light path of the optical resonator, on the basis of the BPF state information (step A4). When the Q switch 55 is turned on, the band pass filter having a transmission wavelength of 750 nm is inserted into the light path of the optical resonator, and thus the laser source unit 13 emits the pulse laser beam having a wavelength of 750 nm.

The pulse laser beam having a wavelength of 750 nm which is emitted from the laser source unit 13 is guided to, for example, the probe 11, and a first partial region of the test object is irradiated with the pulse laser beam from the probe 11. A light absorber absorbs energy of the irradiated pulse laser beam within the test object, and thus a photoacoustic signal is generated. The probe 11 detects the photoacoustic signal generated within the test object. The photoacoustic signal detected by the probe 11 is received by the reception circuit 21.

The trigger control circuit 30 outputs the sampling trigger signal to the AD conversion unit 22 in accordance with the timing at which the Q switch trigger signal is output. The AD conversion unit 22 samples the photoacoustic signal received by the reception circuit 21 with a predetermined sampling period (step A5). The photoacoustic signal sampled by the AD conversion unit 22 is stored as first photoacoustic data in the reception memory 23.

The control unit 31 determines whether a remaining wavelength is present or not, in other words, whether the pulse laser beams of all the predetermined wavelengths to be emitted have been emitted or not (step A6). When a remaining wavelength is present, the process returns to step A2 in order to emit the pulse laser beam having the next wavelength, and the flash lamp trigger signal is output to the laser source unit 13 from the trigger control circuit 30. The flash lamp 52 is turned on in response to the flash lamp trigger signal in step A3, and the trigger control circuit 30 turns on the Q switch 55 in step A4, at the timing when the rotational displacement position of the wavelength selection unit 56 is set to the position where the band pass filter transmitting light having a second wavelength (800 nm) is inserted into the light path of the optical resonator, thereby emitting the pulse laser beam.

The pulse laser beam having a wavelength of 800 nm which is emitted from the laser source unit 13 is guided to, for example, the probe 11, and the first partial region of the test object is irradiated with the pulse laser beam from the probe 11. The probe 11 detects a photoacoustic signal generated by the light absorber within the test object absorbing the pulse laser beam having a wavelength of 800 nm. The trigger control circuit 30 outputs the sampling trigger signal to the AD conversion unit 22 in accordance with the output of the Q switch trigger signal, and the AD conversion unit 22 samples the photoacoustic signal in step A5. The photoacoustic signal sampled by the AD conversion unit 22 is stored as second photoacoustic data in the reception memory 23. The photoacoustic image generation apparatus 10 performs step A1 to step A5 with respect to each wavelength of a pulse laser beam with which the test object is to be irradiated, and irradiates the test object with the pulse laser beam having each wavelength, thereby detecting the photoacoustic signal from the test object.

When the control unit 31 determines in step A6 that a remaining wavelength is not present, the control unit determines whether all the partial regions have been selected or not (step A7). When the partial region to be selected remains, the process returns to step A2. The photoacoustic image generation apparatus 10 performs step A2 to step A6 with respect to each partial region, sequentially irradiates each partial region with pulse laser beams having wavelengths (750 nm and 800 nm), and stores the first photoacoustic data and the second photoacoustic data of each partial region in the reception memory 23. When the irradiation with the pulse laser beam and the detection of the photoacoustic signal have been performed on all the partial regions, photoacoustic data required to generate a photoacoustic image of one frame is gathered.

When the control unit 31 determines in step A7 that all the partial regions have been selected, the process proceeds to the generation of the photoacoustic image. The complex number creation unit 24 reads out the first photoacoustic data and the second photoacoustic data from the reception memory 23, and generates complex number data in which first photoacoustic image data is set to a real part and second photoacoustic image data is set to an imaginary part (step A8). The photoacoustic image reconstruction unit 25 performs image reconstruction from the complex number data generated in step A8, using a Fourier transform method (FTA method) (step A9).

The phase information extraction unit 26 extracts phase information from the reconstructed complex number data (reconstructed image) (step A10). For example, when the reconstructed complex number data is expressed by X+iY, the phase information extraction unit 26 extracts the relation of $\theta=\tan^{-1}(Y/X)$ as the phase information (however, when the relation of X=0 is satisfied, the relation of $\theta=90°$ is satisfied). The intensity information extraction unit 27 extracts intensity information from the reconstructed complex number data (step A11). For example, when the reconstructed complex number data is expressed by X+iY, the intensity information extraction unit 27 extracts $(X^2+Y^2)^{1/2}$ as the intensity information.

The detection and logarithmic transformation unit 28 performs a detection and logarithmic transformation process on the intensity information extracted in step A11. The photoacoustic image construction unit 29 generates a photoacoustic image on the basis of the phase information extracted in step A10 and the performing of the detection and logarithmic transformation process, on the intensity information extracted in step A11 (step A12). For example, the photoacoustic image construction unit 29 generates the photoacoustic image by determining luminance (gradation value) of each pixel in a distribution image of a light absorber on the basis of the intensity information and by determining color of each pixel on the basis of the phase information. The generated photoacoustic image is displayed on the image display unit 14.

In this embodiment, the flash lamp 52 is turned on to excite the laser rod 51 while driving the wavelength selection unit 56 so that the plurality of band pass filters selectively inserted into the light path of the optical resonator are switched at a predetermined speed. After the excitation of the laser rod, when the band pass filter transmitting light having a wavelength of a pulse laser beam to be emitted is inserted into the light path of the optical resonator, the Q switch 55 is turned on. For example, the wavelength selection unit 56 including two band pass filters having different transmission wavelengths are continuously driven, and thus it is possible to continuously and selectively insert the two band pass filters into the light path of the optical resonator and to continuously switch and emit laser beams having a plurality of wavelengths from the laser source unit 13. In addition, the trigger control circuit 30 ascertains a driving state of the wavelength selection unit 56, and turns on the Q switch 55 when the band pass filter having a desired transmission wavelength is inserted into the light path of the optical resonator, and thus it is possible to control the wavelength of the pulse laser beam emitted by the laser source unit 13 from the ultrasonic wave unit 12 side. Furthermore, in this embodiment, the ultrasonic wave unit 12 determines an emission timing of the pulse laser beam, and thus it is not necessary to acquire a signal such as a synchronization signal indicating laser emission from the laser source unit 13, in the start of sampling of a photoacoustic signal.

In this embodiment, complex number data is generated in which one of the first photoacoustic data and the second photoacoustic data which are obtained by irradiating pulse laser beams of two wavelengths is set to a real part and the other is set to an imaginary part, and a reconstructed image is generated from the complex number data using a Fourier transform method. In this case, it is possible to effectively perform the reconstruction as compared with a case where the first photoacoustic data and the second photoacoustic data are separately reconstructed. The pulse laser beams having a plurality of wavelengths are irradiated, and a photoacoustic signal (photoacoustic data) at the time of the irradiation with a pulse laser beam having each wavelength is used, and thus it is possible to perform functional imaging using optical absorption properties of the respective light absorbers being different from each other depending on wavelengths.

In addition, in this embodiment, for example, when a light irradiation region is divided into three partial regions, a first partial region is sequentially irradiated with a pulse laser beam having a first wavelength and a pulse laser beam having a second wavelength, and a second partial region is sequentially irradiated with the pulse laser beam having the first wavelength and the pulse laser beam having the second wavelength, and then a third partial region is sequentially irradiated with the pulse laser beam having the first wavelength and the pulse laser beam having the second wavelength. In this embodiment, any partial region is continuously irradiated with the pulse laser beam having the first wavelength and the pulse laser beam having the second wavelength, and then the next partial region is irradiated. In this case, it is possible to shorten the time from the irradiation with the pulse laser beam having the first wavelength and the irradiation with the pulse laser beam having the second wavelength at the same position, as compared with a case where the three partial regions are irradiated with the pulse laser beam having the first wavelength and are then irradiated with the pulse laser beam having the second wavelength. It is possible to suppress mismatching between the first photoacoustic data and the second photoacoustic data by shortening the time between the irradiation with the pulse laser beam having the first wavelength and the irradiation with the pulse laser beam having the second wavelength.

Figure 5:
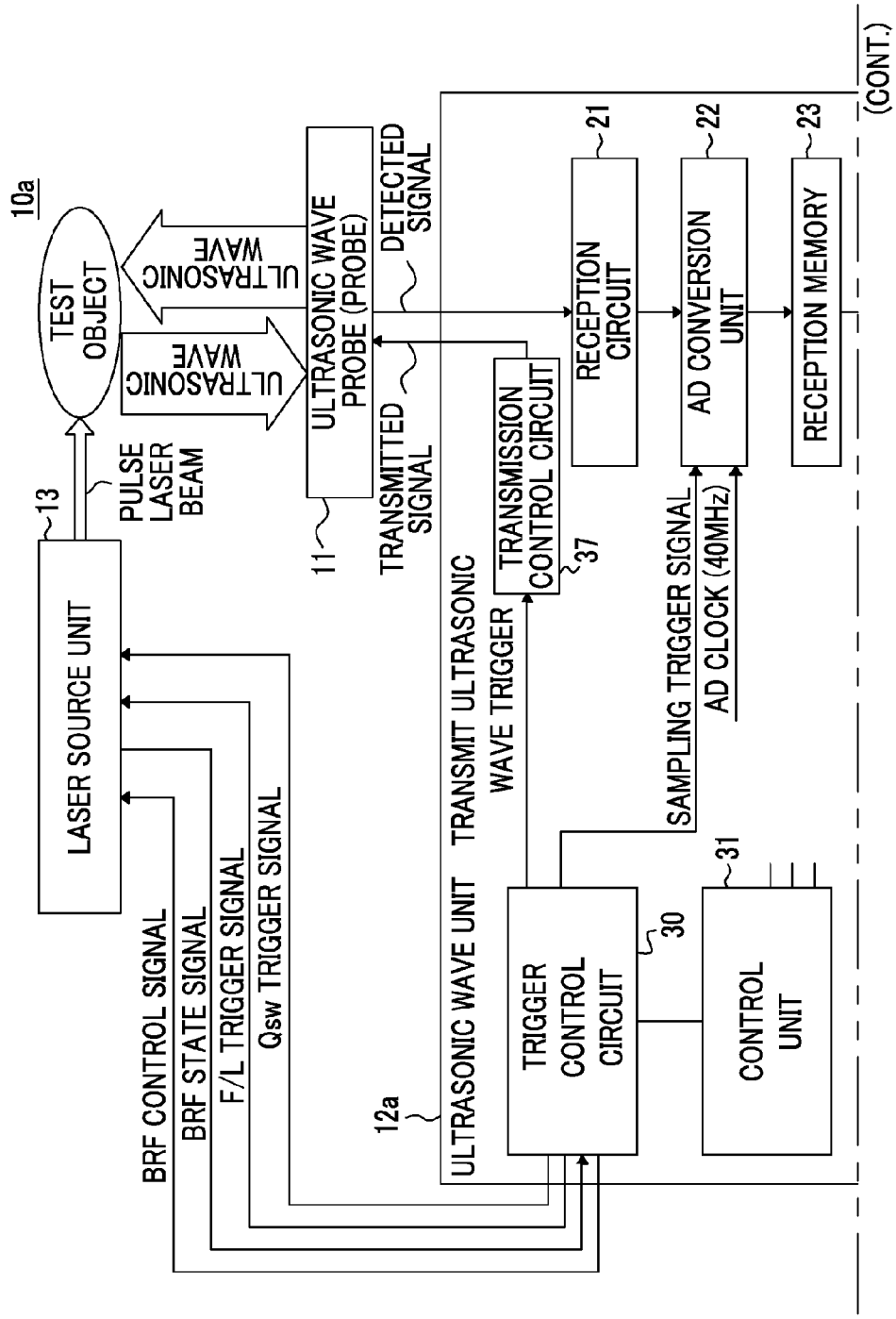
FIG. 5 is a block diagram illustrating a photoacoustic image generation apparatus according to a second embodiment of the present invention.

Subsequently, a second embodiment of the present invention will be described. FIG. 5 illustrates a photoacoustic image generation apparatus according to the second embodiment of the present invention. In a photoacoustic image generation apparatus 10a according to this embodiment, an ultrasonic wave unit 12a includes data separation unit 32, ultrasonic image reconstruction unit 33, detection and logarithmic transformation unit 34, ultrasonic image construction unit 35, image synthesis unit 36, and a transmission control circuit 37, in addition to the configuration of the ultrasonic wave unit 12 in the photoacoustic image generation apparatus 10 according to the first embodiment which is illustrated in FIG. 1. The photoacoustic image generation apparatus 10a according to this embodiment is different from that in the first embodiment in that the apparatus generates an ultrasonic image in addition to a photoacoustic image. Other parts may be the same as those in the first embodiment.

In this embodiment, a probe 11 outputs (transmits) ultrasonic waves to a test object and detects (receives) reflected ultrasonic waves from the test object with respect to the transmitted ultrasonic waves, in addition to the detection of a photoacoustic signal. A trigger control circuit 30 transmits an ultrasonic wave transmission trigger signal for instructing the transmission of ultrasonic waves to the transmission control circuit 37 at the time of the generation of an ultrasonic image. When the transmission control circuit 37 receives the trigger signal, the transmission control circuit causes ultrasonic waves to be transmitted from the probe 11. The probe 11 detects reflected ultrasonic waves from the test object after the transmission of the ultrasonic waves.

The reflected ultrasonic waves detected by the probe 11 are input to AD conversion unit 22 through a reception circuit 21. The trigger control circuit 30 transmits a sampling trigger signal to the AD conversion unit 22 in accordance with the transmission timing of the ultrasonic waves, and starts to sample the reflected ultrasonic waves. The AD conversion unit 22 stores sampling data of the reflected ultrasonic waves (reflected ultrasonic data) in the reception memory 23.

The data separation unit 32 separates the reflected ultrasonic data stored in the reception memory 23 and first and second photoacoustic data from each other. The data separation unit 32 transmits the reflected ultrasonic data to the ultrasonic image reconstruction unit 33, and transmits the first and second photoacoustic data to complex number creation unit 24. The generation of the photoacoustic image on the basis of the first and second photoacoustic data is the same as that in the first embodiment. The data separation unit 32 inputs sampling data of the separated reflected ultrasonic waves to the ultrasonic image reconstruction unit 33.

The ultrasonic image reconstruction unit 33 generates pieces of data of lines of the ultrasonic image on the basis of reflected ultrasonic waves (sampling data thereof) which are detected by a plurality of ultrasonic vibrators of the probe 11. For example, the ultrasonic image reconstruction unit 33 adds data from 64 ultrasonic vibrators of the probe 11 on the basis of a delay time depending on the position of the ultrasonic vibrator to generate data for one line (delay addition method).

The detection and logarithmic transformation unit 34 obtains an envelope of the pieces of data of the lines which are output by the ultrasonic image reconstruction unit 33, and performs logarithmic transformation on the obtained envelope. The ultrasonic image construction unit 35 generates an ultrasonic image on the basis of the data of the lines on which the logarithmic transformation is performed. The ultrasonic image reconstruction unit 33, the detection and logarithmic transformation unit 34, and the ultrasonic image construction unit 35 constitute ultrasonic image generation unit that generates an ultrasonic image on the basis of reflected ultrasonic waves.

The image synthesis unit 36 synthesizes the photoacoustic image and the ultrasonic image. For example, the image synthesis unit 36 performs image synthesis by superimposing the photoacoustic image and the ultrasonic image on each other. At this time, it is preferable that the image synthesis unit 36 perform positioning so that corresponding points of the photoacoustic image and the ultrasonic image are set to be at the same position. The synthesized image is displayed on image display unit 14. It is also possible to display the photoacoustic image and the ultrasonic image on the image display unit 14 side by side without performing image synthesis, or to switch and display the photoacoustic image and the ultrasonic image.

Figure 6:
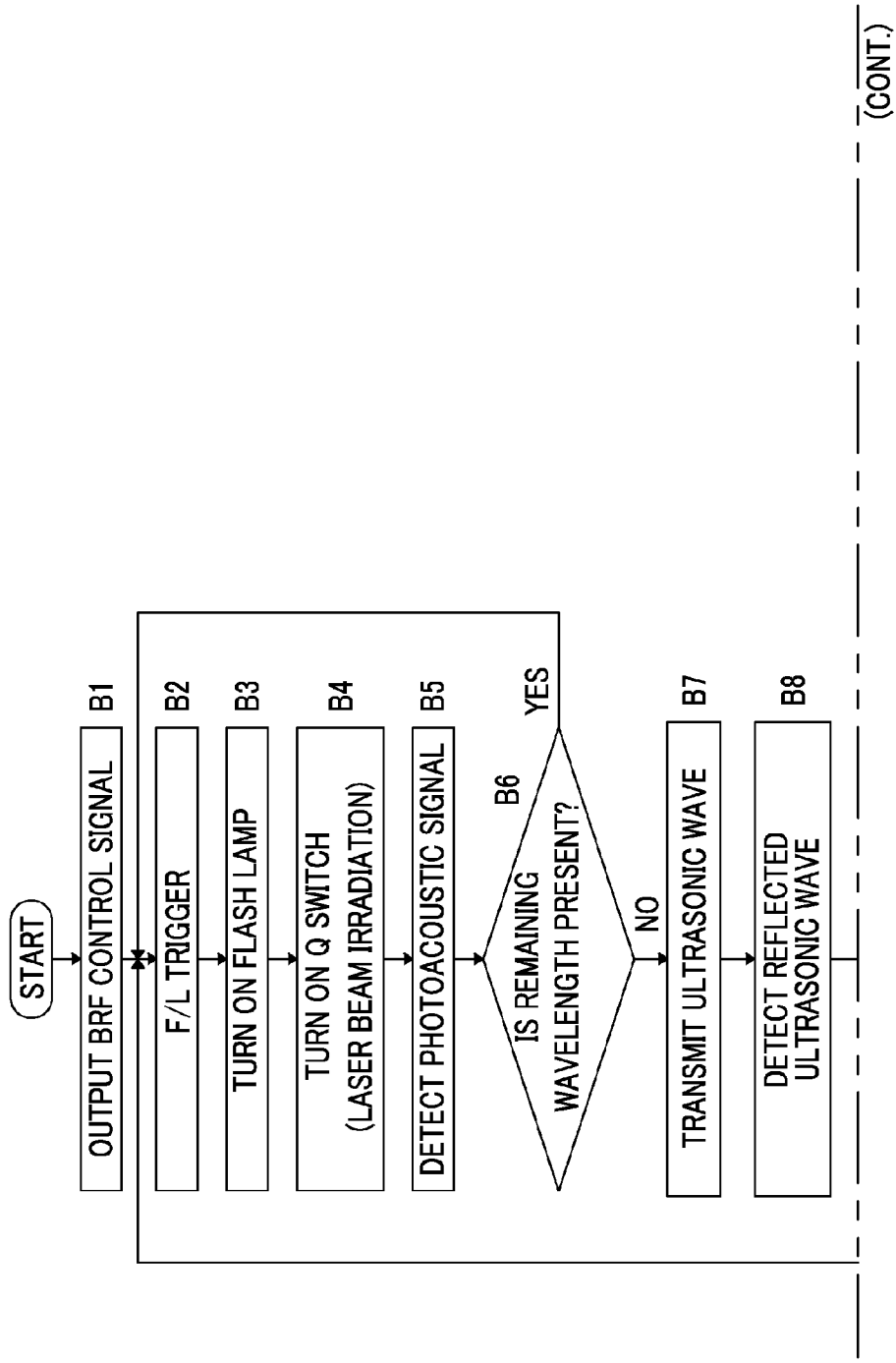
FIG. 6 is a block diagram illustrating an operation procedure of the photoacoustic image generation apparatus according to the second embodiment.

FIG. 6 illustrates an operation procedure of the photoacoustic image generation apparatus 10a. Hereinafter, a description will be given on the assumption that a region of a test object which is irradiated with a laser beam is divided into a plurality of partial regions. The trigger control circuit 30 outputs the BPF control signal for rotating wavelength selection unit (filter rotating body) 56 within a laser source unit 13 at a predetermined rotation speed to the laser source unit 13 (step B1).

When a photoacoustic signal is ready to be received, the trigger control circuit 30 outputs a flash lamp trigger signal in order to emit a pulse laser beam having a first wavelength (for example, 750 nm) (step B2). A flash lamp 52 is turned on in response to the flash lamp trigger signal, and thus a laser rod 51 starts to be excited (step B3).

After the flash lamp 52 is turned on, the trigger control circuit 30 turns on a Q switch 55 at the timing when a rotational displacement position of the wavelength selection unit 56 is set to the position where the band pass filter transmitting light having a wavelength of 750 nm is inserted into a light path of an optical resonator, on the basis of BPF state information. The laser source unit 13 emits a pulse laser beam having a wavelength of 750 nm by the Q switch 55 being turned on.

The pulse laser beam having a wavelength of 750 nm which is emitted from the laser source unit 13 is guided to, for example, the probe 11, and a first partial region of the test object is irradiated with the pulse laser beam from the probe 11. A light absorber absorbs energy of the irradiated pulse laser beam within the test object, and thus a photoacoustic signal is generated. The probe 11 detects the photoacoustic signal generated within the test object. The trigger control circuit 30 outputs a sampling trigger signal to the AD conversion unit 22 in accordance with the output of a Q switch trigger signal. The AD conversion unit 22 receives the photoacoustic signal detected by the probe 11 through the reception circuit 21, and samples the photoacoustic signal with a predetermined sampling period (step B5). The photoacoustic signal sampled by the AD conversion unit 22 is stored as first photoacoustic data in the reception memory 23.

The control unit 31 determines whether a remaining wavelength is present, in other words, whether all the pulse laser beams to be emitted which have a plurality of wavelengths have been emitted (step B6). When a remaining wavelength is present, the process returns to step B2 in order to emit the pulse laser beam having the next wavelength, and the flash lamp trigger signal is output to the laser source unit 13 from the trigger control circuit 30. The flash lamp 52 is turned on in response to the flash lamp trigger signal in step B3, and the trigger control circuit 30 turns on the Q switch 55 in step B4, at the timing when the rotational displacement position of the wavelength selection unit 56 is set to the position where the band pass filter transmitting light having a second wavelength (800 nm) is inserted into the light path of the optical resonator, thereby emitting the pulse laser beam.

The pulse laser beam having a wavelength of 800 nm which is emitted from the laser source unit 13 is guided to, for example, the probe 11, and the first partial region of the test object is irradiated with the pulse laser beam from the probe 11. The probe 11 detects the photoacoustic signal generated by the light absorber within the test object absorbing the pulse laser beam having a wavelength of 800 nm. The trigger control circuit 30 outputs the sampling trigger signal to the AD conversion unit 22 in accordance with the output of the Q switch trigger signal, and the AD conversion unit 22 samples the photoacoustic signal in step B5. The photoacoustic signal sampled by the AD conversion unit 22 is stored as second photoacoustic data in the reception memory 23. The photoacoustic image generation apparatus 10 performs step B1 to step B5 with respect to each wavelength of a pulse laser beam with which the test object is to be irradiated, and irradiates the test object with the pulse laser beam having each wavelength to detect the photoacoustic signal from the test object. Step B1 to step B5 may be the same as step A1 to step A5 of FIG. 4.

When the control unit 31 determines in step B6 that a remaining wavelength is not present, the process proceeds to the transmission and reception of ultrasonic waves. The trigger control circuit 30 transmits the ultrasonic waves to the test object from the probe 11 through the transmission control circuit 37 (step B7). In step B7, the ultrasonic waves are transmitted to the same region as the partial region of the test object which is irradiated with the pulse laser beam. The probe 11 detects reflected ultrasonic waves with respect to the transmitted ultrasonic waves (step B8). The detected reflected ultrasonic waves are sampled in the AD conversion unit 22 through the reception circuit 21, and are stored as reflected ultrasonic data in the reception memory 23.

The control unit 31 determines whether all the partial regions have been selected (step B9). When the partial region to be selected remains, the process returns to step B2. The photoacoustic image generation apparatus 10 performs step B2 to step B6 on each partial region and sequentially irradiates each partial region with pulse laser beams having wavelengths (750 nm and 800 nm) to store the first photoacoustic data and the second photoacoustic data in the reception memory 23. In addition, step B7 and step B8 are performed to store the reflected ultrasonic data in the reception memory 23. When the irradiation with the pulse laser beam, the detection of the photoacoustic signal, and the transmission and reception of the ultrasonic waves have been performed on all the partial regions, data required to generate a photoacoustic image and an ultrasonic image of one frame is gathered.

When the control unit 31 determines in step B9 that all the partial regions have been selected, the process proceeds to the generation of the photoacoustic image and the ultrasonic image. The data separation unit 32 separates the first and second photoacoustic data and the reflected ultrasonic data from each other. The data separation unit 32 transmits the separated first and second photoacoustic data to the complex number creation unit 24, and transmits the reflected ultrasonic data to the ultrasonic image reconstruction unit 33. The complex number creation unit 24 generates complex number data in which first photoacoustic image data is set to a real part and second photoacoustic image data is set to an imaginary part (step B10). The photoacoustic image reconstruction unit 25 performs image reconstruction from the complex number data generated in step B10, using a Fourier transform method (FTA method) (step B11).

The phase information extraction unit 26 extracts phase information from the reconstructed complex number data (step B12). The intensity information extraction unit 27 extracts intensity information from the reconstructed complex number data (step B13). The detection and logarithmic transformation unit 28 performs a detection and logarithmic transformation process on the intensity information extracted in step B 13. The photoacoustic image construction unit 29 generates a photoacoustic image on the basis of the phase information extracted in step B12 and the performing of the detection and logarithmic transformation process, on the intensity information extracted in step B13 (step B14). Here, step B10 to step B14 may be the same as step A8 to step A12 of FIG. 4.

The ultrasonic image reconstruction unit 33 generates pieces of data of lines of the ultrasonic image using, for example, a delay addition method. The detection and logarithmic transformation unit 34 obtains an envelope of the pieces of data of the lines which are output by the ultrasonic image reconstruction unit 33, and performs logarithmic transformation on the obtained envelope. The ultrasonic image construction unit 35 generates an ultrasonic image on the basis of the pieces of data of the lines on which the logarithmic transformation is performed (step B15). The image synthesis unit 36 synthesizes the photoacoustic image and the ultrasonic image and displays the synthesized image on the image display unit 14 (step B16).

In this embodiment, the photoacoustic image generation apparatus generates an ultrasonic image in addition to a photoacoustic image. It is possible to observe a portion not capable of being formed as an image in the photoacoustic image by referring to the ultrasonic image. Other effects are the same as those in the first embodiment.

Note that, in the above-described embodiments, an example in which first photoacoustic data and second photoacoustic data are created as complex numbers has been described, but the first photoacoustic data and the second photoacoustic data may be separately reconstructed without being created as complex numbers. Furthermore, herein, a ratio between the first photoacoustic data and the second photoacoustic data is calculated by the creation of complex numbers and by using phase information, but the same effect is obtained even though the ratio is calculated from intensity information of both the pieces of data. In addition, the intensity information can be generated on the basis of signal intensity in a first reconstructed image and signal intensity in a second reconstructed image.

In the generation of a photoacoustic image, the number of wavelengths of a pulse laser beam with which a test object is to be irradiated is not limited two, and the test object may be irradiated with three or more pulse laser beams, and thus the photoacoustic image may be generated on the basis of pieces of photoacoustic data corresponding to the respective wavelengths. In this case, for example, the phase information extraction unit 26 may generate a magnitude relation between relative signal intensities of the pieces of photoacoustic data corresponding to the respective wavelengths, as phase information. In addition, the intensity information extraction unit 27 may generate the signal intensities in the pieces of photoacoustic data corresponding to the respective wavelengths, which are grouped into one, as intensity information.

Figure 7:
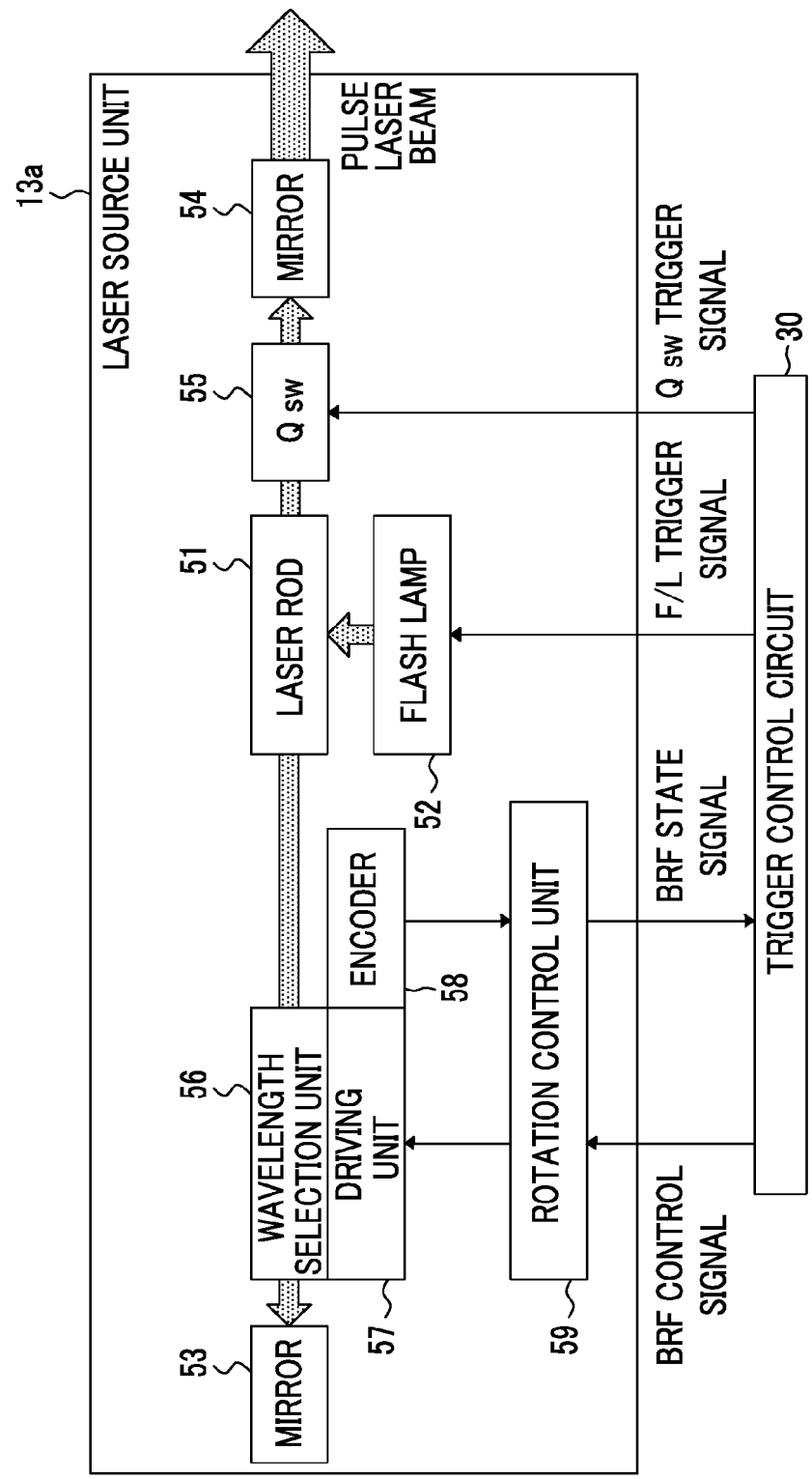
FIG. 7 is a block diagram illustrating a configuration of a laser source unit according to a modified example.

In the above-described embodiments, a description has been made on the assumption that the trigger control circuit 30 monitors BPF state information and controls a rotation speed of the wavelength selection unit 56 (filter rotating body) to be a predetermined rotation speed on the basis of the BPF control signal, but is not limited thereto. FIG. 7 illustrates a modified example of a laser source unit. A laser source unit 13*a* includes a rotation control unit 59 in addition to the configuration of the laser source unit 13 illustrated in FIG. 2. The rotation control unit 59 controls a voltage or the like to be supplied to driving unit 57 so that the amount of rotational displacement which is detected by driving state detection unit 58 during a predetermined period of time is set to an amount according to a predetermined rotation speed of the filter rotating body. The trigger control circuit 30 instructs the rotation control unit 59 on the rotation speed of the filter rotating body on the basis of the BPF control signal. The rotation control unit 59 drives the driving unit 57 so that the rotation speed of the filter rotating body is set to the instructed rotation speed.

In the above-described embodiment, a description has been mainly made of an example in which the wavelength selection unit 56 is constituted by the filter rotating body including two band pass filter regions as illustrated in FIG. 3. However, the wavelength selection unit 56 may be configured to be capable of selectively inserting a plurality of band pass filters having different transmission wavelengths into a light path of an optical resonator, and the present invention is not limited to the configuration of the filter rotating body illustrated in FIG. 3. For example, the wavelength selection unit 56 may be constituted by a rotating body in which a plurality of band pass filters are disposed in a circumferential shape. The wavelength selection unit 56 is not required to be a rotating body, and may be, for example, unit in which a plurality of band pass filters are lined up in a row. In this case, the wavelength selection unit 56 may be driven so that the plurality of band pass filters are cyclically inserted into the light path of the optical resonator, or the wavelength selection unit 56 may be reciprocated so that the plurality of band pass filters lined up in a row cross the light path of the optical resonator.

As described above, although the present invention has been described on the basis of the preferred embodiments, the ultrasonic wave unit and the photoacoustic image generation apparatus of the present invention are not limited to those in the above-described embodiments, and various corrections and modifications made to the configurations of the above-described embodiments may also be included in the scope of the present invention.

What is claimed is:

1. A photoacoustic image generation apparatus comprising:
   a laser source unit capable of emitting a plurality of pulse laser beams having different wavelengths respectively, the laser source unit including a laser rod, an excitation light source that irradiates the laser rod with excitation light, an optical resonator having a pair of mirrors facing each other with the laser rod interposed therebetween, a Q switch which is inserted into the optical resonator, a wavelength selection unit that includes a plurality of band pass filters having different transmission wavelengths and selectively inserts the plurality of band pass filters into a light path of the optical resonator, and a servo motor that drives the wavelength selection unit so that the band pass filters inserted into the light path of the optical resonator are sequentially switched in a predetermined order; and an acoustic wave unit that generates a photoacoustic image, the acoustic wave unit including a detection unit that detects a photoacoustic signal generated within an object when the object is irradiated with the pulse laser beams having the plurality of wavelengths, and generates pieces of photoacoustic data corresponding to the respective wavelengths, an intensity ratio extraction unit that extracts a magnitude relation between relative signal intensities of the pieces of photoacoustic data corresponding to the respective wavelengths, a photoacoustic image construction unit that generates a photoacoustic image on the basis of the extracted magnitude relation, and a trigger control circuit that causes the laser rod to be irradiated with excitation light from the excitation light source while controlling the servo motor, and after the irradiation with the excitation light, turns on the Q switch at a timing when the wavelength selection unit inserts the band pass filter, having a transmission wavelength corresponding to a wavelength of the pulse laser beam to be emitted, into the light path to emit the pulse laser beam, wherein the wavelength selection unit is constituted by a filter rotating body that switches the band pass filter selectively inserted into the light path of the optical resonator in association with rotation, and the servo motor rotationally drives the filter rotating body, the trigger control circuit sends a signal for controlling the servo motor so that the filter rotating body is continuously rotated in a predetermined direction at a predetermined rotation speed, the predetermined rotation speed is determined by the trigger control circuit on the basis of the number of wavelengths of the pulse laser beam to be emitted and the number of times of emission of the pulse laser beam per unit time, the trigger control circuit determines a timing at which irradiation with the excitation light is performed and a timing at which the Q switch is turned on based on filter rotational angle, wherein the filter rotational angle indicates a rotational angle of the filter rotating body obtained by the trigger control circuit and the filter rotational angle is varied in accordance with the rotation of the filter rotating body rotated at the predetermined rotation speed, when the filter rotational angle corresponds to a value representing a position, the trigger control circuit sends a signal to cause the laser rod to be irradiated with excitation light, and the value representing the position is obtained by the trigger control circuit by subtracting a value that corresponds to the amount of rotational displacement of the filter rotating body during a period of time required for the excitation of the laser rod from a value that corresponds to a position of the filter rotating body at which the band pass filter corresponding to a wavelength of the pulse laser beam to be emitted is inserted into the light path.

2. The photoacoustic image generation apparatus according to claim 1, wherein the laser source unit further includes a rotation control unit that sends a signal for controlling the servo motor so that the amount of rotational displacement of the filter rotating body during a predetermined period of time is set to an amount depending on the predetermined rotation speed, and the trigger control circuit controls the servo motor through the rotation control unit.

3. The photoacoustic image generation apparatus according to claim 1,
wherein the acoustic wave unit further includes an intensity information extraction unit that generates intensity information indicating signal intensity on the basis of the pieces of photoacoustic data corresponding to the respective wavelengths, and
wherein the photoacoustic image construction unit determines a gradation value of each pixel of the photoacoustic image on the basis of the intensity information, and determines a display color of each pixel on the basis of the extracted magnitude relation.

4. The photoacoustic image generation apparatus according to claim 3,
wherein the plurality of wavelengths of the pulse laser beams to be emitted by the laser source unit includes a first wavelength and a second wavelength,
wherein the acoustic wave unit further includes a complex number creation unit that generates complex number data in which one of first photoacoustic data corresponding to a photoacoustic signal, detected when irradiation with the pulse laser beam having the first wavelength is performed, and second photoacoustic data corresponding to a photoacoustic signal, detected when irradiation with the pulse laser beam having the second wavelength is performed, is set to a real part and the other one is set to an imaginary part, and a photoacoustic image reconstruction unit that generates a reconstructed image from the complex number data using a Fourier transform method, and
wherein the intensity ratio extraction unit extracts phase information as the magnitude relation from the reconstructed image, and the intensity information extraction unit extracts the intensity information from the reconstructed image.

5. The photoacoustic image generation apparatus according to claim 1,
wherein the detection unit further detects reflected acoustic waves with respect to acoustic waves transmitted to the object to generate reflected acoustic wave data, and
wherein the acoustic wave unit further includes an acoustic wave image generation unit that generates an acoustic wave image on the basis of the reflected acoustic wave data.

* * * * *